(12) United States Patent
Eggen et al.

(10) Patent No.: US 8,124,372 B2
(45) Date of Patent: Feb. 28, 2012

(54) SELECTIVE ENZYMATIC AMIDATION OF C-TERMINAL ESTERS OR ACIDS OF PEPTIDES

(75) Inventors: Ivo Franci Eggen, Oss (NL); Carmen Gabriela Boeriu, Oss (NL)

(73) Assignee: N.V. Organon, Oss (NL)

( * ) Notice: Subject to any disclaimer, the term of this patent is extended or adjusted under 35 U.S.C. 154(b) by 908 days.

(21) Appl. No.: 12/145,100

(22) Filed: Jun. 24, 2008

(65) Prior Publication Data

US 2009/0053760 A1 Feb. 26, 2009

Related U.S. Application Data

(60) Provisional application No. 60/945,982, filed on Jun. 25, 2007.

(51) Int. Cl.
| | |
|---|---|
| *C12P 21/06* | (2006.01) |
| *C12N 9/00* | (2006.01) |
| *C12N 9/50* | (2006.01) |
| *C12N 1/20* | (2006.01) |
| *C12N 15/00* | (2006.01) |
| *C07H 21/04* | (2006.01) |

(52) U.S. Cl. .... 435/68.1; 435/183; 435/219; 435/252.3; 435/320.1; 536/23.2

(58) Field of Classification Search .......... None
See application file for complete search history.

(56) References Cited

U.S. PATENT DOCUMENTS 6,864,357 B2  3/2005  Eggen et al.

FOREIGN PATENT DOCUMENTS

| EP | 1291356 A2 | 3/2003 |
|---|---|---|
| EP | 1291356 A3 | 3/2003 |
| EP | 1291356 B1 | 3/2003 |

OTHER PUBLICATIONS

Chen, S.T. et al, Facile Amide Bond Formation from Esters of Amino Acids and Peptides Catalyzed by Alkaline Protease in Anhydrous tert-Butyl Alcohol using Ammonium Chloride/Triethylamine as a Source of Nucleophilic Ammonia, Synthesis, vol. 09, pp. 858-860, (1993).
Klein, J.U. et al.; "The Applicability of Subtilisin Carlsberg in Peptide Synthesis" Journal of Peptide Science, vol. 6, No. 11, pp. 541-549, (2000).
PCT International Search Report dated Sep. 30, 2008 for corresponding PCT Application No. PCT/EP2008/057972.
European Search Report dated Dec. 3, 2007 for corresponding EP Application No. 07012410.2-1521.
Carpino et al, "The 2,2,4,6,7-Pentamethyldihydrobenzofuran-5-Sulfonyl Group (Pbf) as Arginine Side Chain Protectant," Tetrahedron Letters, vol. 34, No. 49, pp. 7829-7832 (1993).
Carpino et al, "Novel Carboxylic Acid and Carboxamide Protective Groups Based on the Exceptional Stabilization of the Cyclopropylmethyl Cation," J. Org. Chem, vol. 60, pp. 7718-7719 (1995).
Carreño et al, "Nsc and Fmoc N$^\alpha$-amino Protection for Solid-Phase Peptide Synthesis: A Parallel Study," Peptide Res., vol. 56, pp. 63-69 (2000).
Čeřovský et al, "C-Terminal Peptide Amidation Catalyzed by Orange Flavedo Peptide Amidase," Angew. Chem. Int. Ed., vol. 37, No. 13/14, pp. 1885-1887(1998).
Čeřovský et al, "Studies on Peptide Amidase-Catalysed C-Terminal Peptide Amidation in Organic Media with Respect to its Substrate Specificity," Biotechnol. Appl. Biochem., vol. 33, pp. 183-187 (2001).
Cunningham et al, "Muramyl Peptide Analogs: Synthesis of a Depsipeptide Using Orthogonal SPPS," Tetrahedron Letters, vol. 35, No. 51, pp. 9517-9520 (1994).
De Zoete et al, "Lipase-Catalysed Ammoniolysis of Lipids. A Facile Synthesis of Fatty Acid Amides," Journal of Molecular Catalysis B: Enzymatic 1, pp. 109-113 (1996).
Eggen et al, "Diosynth Rapid Solution Synthesis of Peptides," Organic Process Research & Development, vol. 9, No. 1, pp. 98-101 (2005).
Eggen et al, "A Novel Method for Repetitive Peptide Synthesis in Solution Without Isolation of Intermediates," Journal of Peptide Science, vol. 11, pp. 633-641 (2005).
Franzén et al, "Synthesis, Properties, and Use of Nin-Boc-tryptophan Derivatives," J. Chem. Soc., Chem. Commun., pp. 1699-1700 (1984).
Kulathila et al, "Enzymatic Formation of C-Terminal Amides," Nat. Prod. Rep., vol. 16, pp. 145-154 (1999).
Liltjens et al, "Exploration of Lipase-Catalyzed Direct Amidation of Free Carboxylic Acids with Ammonia in Organic Solvents," Tetrahedron, vol. 55, pp. 12411-12418 (1999).
Masuda et al, Studies on the Solvent Dependence of the Carbamic Acid Formation from ω-(1-Naphthyl)Alkylamines and Carbon Dioxide, Tetrahedron, vol. 61, pp. 213-229 (2005).
Maugard et al, "Enzymatic Synthesis of Glycamide Surfactants by Amidification Reaction," Tetrahedron, vol. 53, No. 14, pp. 5185-5194 (1997).
McMurray, Solid Phase Synthesis of a Cyclic Peptide Using Fmoc Chemistry, Tetrahedron Letters, vol. 32, No. 52, pp. 7679-7682 (1991).
Mergler et al, "The Aspartimide Problem in Fmoc-Based SPPS. Part I," Journal of Peptide Science, vol. 9, pp. 36-46 (2003).
Ramage et al, N$_G$-2,2,5,7,8-Pentamethylchroman-6-Sulphonyl-I-Arginine: A New Acid Labile Derivative for Peptide Synthesis, Tetrahedron Letters, vol. 28, No. 20, pp. 2287-2290 (1987).
Reyes-Duarte et al, "Lipase-Catalysed Synthesis of Olvanil in Organic Solvents," Biotechnology Letters, vol. 24, pp. 2057-2061 (2002).
Sakakibara et al, "Use of Anhydrous Hydrogen Fluoride in peptide Synthesis. I. Behavior of Various Protective Groups in Anhydrous Hydrogen Fluoride", Chem. Soc. Jpn., vol. 40, pp. 2164-2167 (1967).
Sánchez et al, *Candida antarctica* Lipase-Catalyzed Doubly Enantioselective Aminolysis Reactions. Chemoenzymatic Synthesis of 3-Hydroxypyrrolidines and 4-(Silyloxy)-2-oxopyrrolidines with Two Stereogenic Centers, J. Org. Chem., vol. 64, pp. 1464-1470 (1999).

(Continued)

*Primary Examiner* — Christian Fronda

(57) ABSTRACT

The present invention relates to a process for the amidation of C-terminal esters or acids of peptide substrates in solution-phase synthesis of peptides, comprising amidating one or more peptide substrates comprising C-terminal esters or acids using the protease subtilisin in any suitable form in the presence of an ammonium salt derived from an acid having a pKa above 0.

This process is useful in the production of protected or unprotected peptides.

27 Claims, No Drawings

OTHER PUBLICATIONS

Shimonishi et al, "Studies on the Synthesis of Peptides Containing Glutamine as the C-Terminal. I. Protection of Amide-Nitrogen with Xanthyl Group During Peptime Synthesis," Bull. Chem. Soc. Jpn., vol. 35, pp. 1966-1970 (1962).

Sieber, "The 2-Trimethylsilylethyl Residue, A Selectively Cleavable Carboxyl Protecting Group," Helvetica Chimica Acta, vol. 60, Issue 8, pp. 2711-2716 (1977) [Abstract].

Sieber et al, "Protection of Histidine in Peptide Synthesis: A Reassessment of the Trityl Group," Tetrahedron Letters, vol. 28, No. 48, pp. 6031-6034 (1987).

Sieber et al, "Protection of Carboxamide Functions by the Trityle Residue, Application to Peptide Synthesis," vol. 32, No. 6, pp. 739-742 (1991).

Torre et al, Study of the Chemoselectivity in the Aminolysis Reaction of Methyl Acrylate catalysed by Lipase B from *Candida antarctica*, Adv. Synth. Catal., vol. 347, pp. 1007-10014 (2005).

Weygand et al, "Vergleichende Untersuchungen zur Abspaltung substit. Benzylreste vom Amidstickstoff und deren Kombinationsmöglichkeiten mit Urethanschutzgruppen," Chem. Ber., vol. 101, pp. 3623-3641 (1968).

"Protection of Functional Groups in Peptide Synthesis," The Peptides Academic Press, vol. 3 Analysis, Synthesis, Biology, Gross and Meienhofer eds. (1981).

SELECTIVE ENZYMATIC AMIDATION OF C-TERMINAL ESTERS OR ACIDS OF PEPTIDES

This application claims the benefit of U.S. Provisional Patent Application No. 60/945,982, filed Jun. 25, 2007.

The invention relates to a process for selective enzymatic amidation of C-terminal esters or acids of peptide substrates in solution-phase synthesis of peptides.

Many biologically active peptides contain a C-terminal primary amide function, e.g. gonadorelin, oxytocin, and arginine vasopressin. There are several strategies for the synthesis of peptide amides in solution, which can be roughly divided into four different categories.

In the most straightforward approach, synthesis is started from the free C-terminal amino acyl amide, maintaining the amide in its free form during the entire synthesis. Although the most obvious approach on first examination, syntheses in solution in the presence of a free amide function on the growing peptide chain are often fraught with serious solubility problems due to hydrogen bonding. Moreover, for peptide synthesis on a manufacturing scale, the DioRaSSP® method is particularly preferred (EP-A-1,291,356; U.S. Pat. No. 6,864,357; Eggen I. et al., *Org. Process Res. Dev.* 2005, 9, 98-101; Eggen I. et al., *J. Peptide Sci.*, 2005, 11, 633-641). In this method, the growing peptide chain is more or less anchored in a permanent organic phase. However, when using a free amide function, there is a significant risk of losing a substantial portion of the growing peptide during aqueous washings, especially in the earlier cycles of the synthesis.

In order to circumvent the aforementioned solubility problems, the amide function may be protected during the synthesis, hence starting from the C-terminally protected amino acyl amide. This approach also ensures the anchoring of the growing peptide in the organic phase. Protecting groups for the amide function may be selected from benzyl (Weygand, F. et al., *Chem. Ber.*, 1968, 101, 3623-3641), benzhydryl (Sakakibara, S. et al., *Bull. Chem. Soc. Jpn.*, 1967, 40, 2164-2167), triphenylmethyl (Sieber, P. et al., *B., Tetrahedron Lett.*, 1991, 32, 739-742), xanthenyl (Shimonishi, Y. et al., *Bull. Chem. Soc. Jpn.*, 1962, 35, 1966-1970), and cyclopropylmethyl type moieties (Carpino, L. A. et al., *J. Org. Chem.*, 1995, 60, 7718-7719), whose lability towards acid is determined by the substituents attached to this moiety. A general problem is the poor accessibility and commercial availability of the starting amino acid derivatives, especially if these contain protected side chains. Moreover, cleavage of the protecting group from the amide function under acidic conditions may result in the formation of alkylated analogues, depending on the actual sequence of the peptide, the conditions for deprotection and the nature of the protecting group.

A third option for the synthesis towards peptides with a C-terminal amide function is to start from amino acyl esters, which allow selective cleavage towards the free carboxylic function in the presence of acid-labile protecting groups on the side chains of the peptide. The free carboxylic function is subsequently activated to allow reaction with ammonia c.q. ammonium. Esters within the scope of this approach include 9-fluorenylmethyl (Fm) (Cunningham, B. R. et al., *Tetrahedron Lett.*, 1994, 35, 9517-9520) and 2-(4-nitrophenylsulfonyl)ethyl (Nse) esters (Carreno, C. et al., *J. Peptide Res.*, 2000, 56, 63-69) which are cleaved under basic conditions, 2-(trimethylsilyl)ethyl (Trmse) esters which are cleaved by fluoridolysis (Sieber, P., *Helv. Chim. Acta*, 1977, 60, 2711-2716), and 2,4-dimethoxybenzyl (Dmb) esters which are cleaved by mild acidolysis (McMurray, J. S., *Tetrahedron Lett.*, 1991, 32, 7679-7682). The main problem with this approach is that it comprises two potential racemization-inducing steps of the C-terminal amino acid derivative, i.e. the esterification step and the actual amidation step. Moreover, the cleavage step may lead to side reactions within the peptide sequence, such as conversion of internal Asp(OBu$^t$) residues to the succinimide under basic (Mergler, M. et al., *J. Pept. Sci.*, 2003, 9, 36-46) or fluorodolytic conditions. Finally, the ester function itself may not be completely stable during the assembly of the peptide sequence; e.g., benzyl-type esters (Fm and Dmb) are cleaved during hydrogenolysis, thus ruling out the use of the benzyloxycarbonyl (Z) group for temporary protection of the amino function.

The last option for the synthesis towards peptides with a C-terminal amide function is to start from simple primary amino acyl esters, such as methyl, ethyl or benzyl esters, which are at a later stage converted to the amides via direct ammonolysis. These are in general widely available and easily accessible starting compounds. However, this approach is limited by the fact that the ammonolytic conditions also induce side reactions within the peptide sequence, such as racemization and conversion of internal Asp(OBu$^t$) residues to the succinimide.

It may be concluded that the use of simple primary amino acyl esters as the starting materials in the synthesis towards peptides with a C-terminal amide function is preferred, if the chemical ammonolysis can be replaced by a mild selective method for the amidation.

Enzymatic methods have gained interest in peptide synthesis during the past couple of years. Enzymes often show high chemo-, regio- and stereoselectivity. Furthermore, enzymes usually operate under very mild conditions, at neutral pH values and at temperatures of 20-50° C. Thus, under such conditions, side reactions can be circumvented.

In mammals several amidating enzymes are expressed, including bifunctional Peptidylglycine α-Amidating Monooxygenase (PAM) and the monofunctional enzymes Peptidyl α-Hydroxylating Monooxygenase (PHM) and Peptidyl Amidoglycoiate Lyase (PAL) (Kulathila, R. et al., *Nat. Prod. Rep.*, 1999, 16, 145-154). These enzymes need a glycine at the C-terminus and are therefore not generally applicable. Furthermore, these isolated enzymes are very costly and have found no application in the laboratory (Čeřovský, V. et al., *Biotechnol. Appl. Biochem.*, 2001, 33, 183-187).

Čeřovský et al. reported (Čeřovský, V. et al., *Angew. Chem. Int. Ed.*, 1998, 37, 1885-1887) the application of an enzyme isolated from orange peel in the amidation of the free acid of a C-terminal peptide. Despite some optimization yields never exceeded 35%. Furthermore, in another publication the yields seemed to be largely dependant on the substrate used (Čeřovský, V., Kula, M. R., *Biotechnol. Appl. Biochem.*, 2001, 33, 183-187). Finally, the Čeřovský method is based on conversion of peptide with a free C-terminal acid to the corresponding amide. Since solution-phase synthesis usually yields a C-terminal ester, an additional synthesis step is required to deprotect the ester function. Accordingly, it will be very difficult to apply this orange peel enzyme in an industrial process.

The use of lipases has shown a wide spread application in organic chemistry. Several publications report the use of *Candida antarctica* lipase in the amidation of organic compounds, resulting in substituted and non-substituted amides (Reyes-Duarte, D. et al., Biotech Lett., 2002, 24, 2057-2061; Sánchez, V. M. et al., J. Org. Chem. 1999, 64, 1464-1470; Torre, O. et al., *Adv. Synth. Catal.* 2005, 347, 1007-1014; Maugard, T. et at., Tetrahedron, 1997, 53, 14, 5185-5194; Zoete de, M. C. et al., Sheldon, R. A. *Journal Molecular Catalysis B: Enzymatic*, 1996, 1, 109-113; Litjens, M. J. J. et al., Tetrahedron, 1999, 55, 12411-12418). The application of this enzyme in peptide chemistry however remains to be reported.

Finally, Chen S-T. et al., *Synthesis,* 1993, 858-860, reports the enzymatic amidation of esters of amino acids and C-terminal peptide esters with Alcalase (free subtilisin) in the presence of ammonium chloride/triethyl amine at pH 10.6 and higher. Reported yields are between 50 and 70%. Chen reports in a table the amidation of a dipeptide with a 68% conversion in 12 hours. The amidation of a tripeptide is also reported. However, the conversion is not listed. It may also be mentioned here that it is highly undesired in solution-phase synthesis of peptide to use such high pH as this might result in the destruction of the peptide. Therefore, mild conditions, i.e. a pH of 10 or lower, are preferred.

Therefore, despite these positive developments enzymatic amidation of the C-terminal ester of a peptide by means of a commercially available enzyme with high yields remains a daunting challenge hitherto.

A new process has now been found for the amidation of C-terminal esters or acids of peptide substrates in solution-phase synthesis of peptides, comprising amidating one or more peptide substrates comprising C-terminal esters or acids using the protease subtilisin in any suitable form in the presence of an ammonium salt derived from an acid having a pKa above 0.

Surprisingly, it has been found that with the process of the present invention high yields of the amidated product can be obtained, while endopeptidase activity is substantially suppressed.

With C-terminal acids of peptide substrates is meant the free C-terminal acid of a peptide.

Preferred are the C-terminal esters of peptide substrates. Since solution-phase synthesis usually yields a C-terminal ester, an additional synthesis step is required to deprotect the ester function. Furthermore, the amidation of the free C-terminal acid of a peptide is much slower than the amidation of the C-terminal ester.

The esters of the C-terminal esters of the peptide substrate may be selected from the group of $C_{1-12}$ (ar)alkyl esters, e.g. methyl, ethyl, propyl, butyl, and benzyl esters, in particular primary $C_{1-12}$ (ar)alkyl esters, preferably primary $C_{1-4}$ alkyl esters, more preferably ethyl and methyl esters. The C-terminal methyl ester of the peptide substrate is the most preferred embodiment.

The ammonium salt is derived from an acid having a pKa above 0, preferably from an acid having a pKa above 3.5, most preferably, having a pKa between 3.5 and 7. Examples include diammonium hydrogen phosphate, ammonium dihydrogen phosphate, ammonium fluoride, or ammonium sulphite hydrate.

Alternatively, the ammonium salt may have the following chemical structure (i):

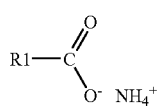

(I)

wherein
R1 is selected from the group of hydrogen, $C_{1-12}$ (ar)alkyl, $C_{6-12}$ aryl, $—N(R2)_2$, $—OH$, and $R3-O^-NH_4^+$,
R2 is selected from the group of hydrogen and/or $C_{1-4}$ alkyl, and
R3 is a bond, a carbonyl group, or a $C_{1-4}$ alkyl carbonyl group, optionally substituted with one or more hydroxyl groups and/or $—COO^-NH_4^+$,
optionally in hydrated form.

Examples of ammonium salts according to the above-mentioned formula include ammonium carbamate, ammonium acetate, ammonium tartrate, ammonium benzoate, ammonium citrate, ammonium formate, ammonium oxalate monohydrate, ammonium carbonate, ammonium bicarbonate, and mixtures thereof.

Preferably, R1 is selected from the group of $C_{1-12}$ (ar)alkyl, $C_{6-12}$ aryl, $—NH_2$, $—OH$, and $—O^-NH_4^+$.

Preferred embodiments are selected from ammonium carbamate, ammonium carbonate, ammonium bicarbonate, ammonium acetate, ammonium benzoate, and mixtures thereof.

Ammonium carbamate is the most preferred embodiment.

It is understood that ammonium carbamate cannot be derived in practice from carbamic acid in view of the fact that carbamic acid as such is an unstable compound and thus therefore does not exist. However, for the sake of the present invention it is defined that ammonium carbamate is an ammonium salt derived from carbamic acid, having a pKa between 4.2 and 7 (Masuda K. et al., *Tetrahedron,* 2005, 61, 213-229).

The protease subtilisin (EC 3.4.21.62) may be used in the process of the invention in any form, thus it may be used in soluble and/or crystallized form, but also in immobilized form or other insoluble form, e.g. in the form of cross-linked enzyme aggregates (CLEA) or cross-linked enzyme crystals (CLEC).

The new process of this invention may conveniently be used in the production of protected or unprotected peptides.

Preferably, the C-terminal ester or acid of the peptide substrates comprises a C-terminal acyl residue which is an α-amino acyl residue from natural or synthetic origin. The C-terminal α-amino acyl residue may be protected or unprotected at the side chain. In particular preferred are C-terminal α-amino acyl residues selected from Ala, protected Cys, protected Asp, protected Glu, Phe, Gly, His, (protected) Lys, Leu, Met, Asn, Gln, (protected) Arg, (protected) Ser, Thr, Val, (protected) Trp and (protected) Tyr, wherein the brackets around the word "protected" mean that the residue can be present in both side-chain protected and unprotected form. The three-letter code for amino acids is used here according to IUPAC nomenclature (IUPAC-IUB Commission (1985) *J. Biol. Chem.* 260, 14-42).

In a further preferred embodiment, protected or unprotected peptide substrates used in the process of this invention are prepared according to DioRaSSP®. Thus, a peptide substrate comprising a C-terminal ester or acid is preferably prepared according to this process for rapid solution synthesis of a peptide in an organic solvent or a mixture of organic solvents, the process comprising repetitive cycles of steps (a)-(d):

(a) a coupling step, using an excess of an activated carboxylic component to acylate an amino component,
(b) a quenching step in which a scavenger is used to remove residual activated carboxylic functions, wherein the scavenger may also be used for deprotection of the growing peptide,
(c) one or more aqueous extractions and
optionally, (d) a separate deprotection step, followed by one or more aqueous extractions, whereby in at least one cycle in process step b an amine comprising a free anion or a latent anion is used as a scavenger of residual activated carboxylic functions. The amine is preferably benzyl β-alaninate or a salt thereof.

The molar ratio of ammonium salt to peptide substrate may range from 2:1 to 20:1, preferably 5:1 to 12:1, more preferably 6:1 to 10:1.

The amidation of the process of the present invention may be performed in one or more organic solvents. Polar organic solvents are preferred, and in particular the organic solvent is selected from N,N-dimethylformamide (DMF), N-methyl-2-pyrrolidone (NMP), dioxane, N,N-dimethylacetamide (DMA), dichloromethane (DCM), tetrahydrofuran (THF), acetonitrile, tert-butanol, tert-amyl alcohol, dichloroethane (DCE), tert-butyl methyl ether (MTBE), and mixtures thereof. Preferred are mixtures of tert-butanol and DMF, tert-butanol and NMP, tert-amyl alcohol and DMF, or tert-amyl alcohol and NMP.

These mixtures may be used in a ratio of 40:60 to 95:5 (v/v), preferably 60:40 to 90.10 (v/v), more preferably in a ratio of 82.5:17.5 (v/v).

Preferably, a small amount of water is present in the reaction mixture. It has been found that in a fully anhydrous "dry" system the enzyme is inactivated due to lack of water. However, when the water concentration is too high in the reaction mixture undesired ester hydrolysis occurs to a significant extent (i.e. formation of a C-terminal free acid) at the cost of amidation. Accordingly, the percentage of water in the mixture may range from 0.0001 to 5% (v/v), preferably from 0.01 to 2% (v/v). It is especially useful when the percentage of water in the mixture is about 0.1 to 1% (v/v).

Water may be added on purpose or by introducing water-containing reagents. For example, when cross-linked enzyme aggregates (CLEA's) are used, water is introduced automatically in the reaction mixture due to its presence in CLEA's.

Introduction of water in the reaction mixture may be carried out in the form of an aqueous buffer. Suitable buffers may be selected from buffers which are generally used for transformations using proteolytic enzymes. In particular, the aqueous buffer is a phosphate, borate or 2-amino-2-hydroxymethyl-1,3-propanediol (TRIS) buffer.

The pH at which the reaction is performed may be selected from the range of 5.5-10, preferably 5.5-8.5, more preferably 6-8, and most preferably the pH is 7.

Reaction temperatures for the amidation may suitably be selected in the range of 15-60° C., in particular 20 to 40° C. Preferred is a reaction temperature of 30° C.

The amount of enzyme may suitably be selected in the range of 1 to 50 wt. % of enzyme related to the peptide substrate, preferably 5 to 10 wt. %.

In a further embodiment of the invention, the amidation is performed by stepwise adding portions of the protease subtilisin (in any suitable form) to the reaction mixture comprising one or more peptide substrates comprising C-terminal esters or acids.

In an alternative embodiment of the invention, the amidation is performed by stepwise adding portions of the ammonium salt to the reaction mixture comprising one or more peptide substrates comprising C-terminal esters or acids.

The peptide substrates, of which the C-terminal esters or acids are amidated in the process of the invention, may carry protecting groups in other parts of their peptide sequence.

The amidation can be carried out with one peptide substrate as well as a mixture thereof. Such a mixture may comprise peptide substrates having only C-terminal esters, peptide substrates having only free C-terminal acids, or peptide substrates having both C-terminal esters and free C-terminal acids.

A suitable process according to the present invention is as follows.

To a solution of a C-terminal ester or acid of a peptide substrate in a suitable organic solvent (or mixture of organic solvents) ammonium salt is added. The reaction mixture is incubated above ambient and the reaction is started by the addition of an enzyme catalyst. The enzyme can be added in solution (e.g. Subtilisin A in phosphate buffer), in suspension or as solid material (e.g. native enzyme, immobilised enzyme or cross-linked enzyme). When substrate conversion has reached a desired level, e.g. higher than 90%, the peptide may be isolated according to the knowledge of the skilled person.

The term 'substrate' herein means an entity which is converted to a product by the protease subtilisin in any form. This product may be a final peptide product whereby if present only the protected functional side chains have still to be deprotected. Alternatively, this product may also be a peptide fragment which subsequently is reacted with other peptide fragments in a convergent synthesis to obtain a longer peptide with the required final number of amino acids.

A person skilled in the art can easily identify suitable substrates, for instance by performing a simple test amidation of a selected peptide comprising a C-terminal ester functionality or a free C-terminal acid under suitable conditions as described herein before and following conversion e.g. by HPLC techniques.

It is established that the process is very suitable to prepare amides of short peptides comprising up to 5 amino acids. Furthermore, a skilled person will also be able to prepare longer peptides. Peptides may also be prepared with D-amino acids.

The term 'protected' means that the functional groups (within the peptide) are protected with suitable protecting groups. A person skilled in the art will know which type of protection to select for which type of functional group. For example, amine functions present in the compounds may be protected during the synthetic procedure by an N-protecting group, which means a group commonly used in peptide chemistry for the protection of an α-amino group, like the tert-butyloxycarbonyl (Boc) group, the benzyloxycarbonyl (Z) group, or the 9-fluorenylmethyloxycarbonyl (Fmoc) group. Overviews of amino protecting groups and methods for their removal is given in Geiger R. and König W. (1981) in *Peptides: Analysis, Synthesis, Biology*, Vol 3, Gross E. and Meienhofer, J., eds, Academic Press, New York, pp. 1-99, and *Peptides: Chemistry and Biology*, Sewald N. and Jakubke H.-D., eds, Wiley-VCH, Weinheim, 2002, pp. 143-154. Functions of the tert-butyl type or functions of similar lability are preferred for the protection of other functional groups on the side chains; these include—but are not limited to—tert-butyl (Bu$^t$) for the protection of the Asp, Glu, Ser, Thr and Tyr side chains, tert-butoxycarbonyl (Boc) for the protection of the Lys and Trp side chains, trityl (Trt) for the protection of the Asn, Gln and His side chains and 2,2,5,7,8-pentamethylchromane-6-sulfonyl (Pmc) or 2,2,4,6,7-pentamethyldihydrobenzofurane-5-sulfonyl (Pbf) for the protection of the Arg side chain [Barany, G. and Merrifield, R. B. (1980) in: '*The Peptides*', vol. 2 (Gross, E. and Meienhofer, J., eds.) Academic Press, New York, pp. 1-284; for Trp(Boc): Franzén, H. et al. (1984) *J. Chem. Soc., Chem. Commun.*, 1699-1700; for Asn (Trt) and Gln(Trt): Sieber, P. et al. (1991) *Tetrahedron Lett.* 32, 739-742; for His(Trt). Sieber, P. et al. (1987) *Tetrahedron Lett.* 28, 6031-6034; for Pmc: Ramage, R. et al. (1987) *Tetrahedron Lett.* 28, 2287-2290; for Pbf: Carpino, L. A. et al. (1993) *Tetrahedron Lett.* 34, 7829-7832].

The invention is further illustrated by the following examples, which is not to be interpreted as a limitation of this invention.

EXAMPLES

The peptides have been produced according to conventional solution phase methods for peptide synthesis.

The free enzyme Subtilisin A was purchased from Novozymes unless otherwise stated. Alcalase CLEA, Savinase CLEA, and CAL-B CLEA were obtained from CLEA Technologies B.V., Delft, The Netherlands. All other enzymes were purchased from Sigma Aldrich.

| | |
|---|---|
| P—NH$_2$ = | Z-peptide-NH$_2$, e.g. Z-Val-Phe-NH$_2$ |
| P—OH = | Z-peptide-OH, e.g. Z-Val-Phe-OH |
| P—OMe = | Z-peptide-OMe, e.g. Z-Val-Phe-OMe |
| Bu$^t$OH = | tert-butanol |
| Am$^t$OH = | tert-amyl alcohol |
| DMF = | N,N-dimethylformamide |
| NMP = | N-methyl-2-pyrrolidone |
| DMA = | N,N-dimethylacetamide |
| DCM = | dichloromethane |
| THF = | tetrahydrofuran |
| DCE = | dichloroethane |

Example 1 and Comparative Examples A-G

General Procedure for Screening the Effect of Enzyme

A stock solution of Z-Ala-Phe-OMe in DMF (200 mM) was prepared. 0.5 mmol of ammonium carbamate was added to 0.25 ml of the dipeptide stock solution. Next, 0.625 ml DMF and 4.125 ml Bu$^t$OH was added. Depending on the enzyme used 10 μl phosphate buffer 0.1 M pH 7.0 was added. The reaction mixture was incubated at 30° C. and the reaction was started by the addition of approximately 20 mg of enzyme. A sample (2 ml) was taken after two hours. 2 ml of acetonitrile was added and the mixture was centrifuged. The supernatants were analyzed by HPLC. The results are shown in Table 1.

TABLE 1

| Ex. | H$_2$O/Bu$^t$OH/DMF | Z-Ala-Phe-NH$_2$ a/a % | Z-Ala-Phe-OH a/a % | Z-Ala-Phe-OMe a/a % | Enzyme |
|---|---|---|---|---|---|
| 1 | 0.2/82.5/17.5 | 86.2 | 13.4 | 0.4 | Alcalase CLEA |
| A | 0.2/82.5/17.5 | 5 | 2.6 | 92.4 | Savinase CLEA |
| B | 0.2/82.5/17.5 | 0 | 0 | 100 | CAL-B CLEA |

As is seen from the results in Table 1 *Candida Antartica* Lipase-B CLEA (CAL-B CLEA) and Savinase-CLEA are not active.

In similar protocols as described above Carboxypeptidase A (Comp. Ex. C), Lipase CC (*Candida Cylindracea*) (Comp. Ex. D), Lipase CR (*Candida Rugosa*) (Comp. Ex. E), Esterase HL (hog liver) (Comp. Ex. F), and Lipase CA (AR) (CAL-B immobilized on acrylic resin) (Comp. Ex. G) were not active. The reaction mixtures were also analyzed after 16 hours, providing similar results.

Examples 2 and 3 and Comparative Example H

General Procedure for Screening the Effect of Ammonium Source

A stock solution of Z-Ala-Phe-OMe in DMF (50 mM) was prepared. 0.5 mmol of the ammonium source was added to 1 ml of the dipeptide stock solution. 4 ml Bu$^t$OH was added. 50 μl phosphate buffer 0.1 M pH 7.6 was added. The reaction mixture was incubated at 40° C. and the reaction was started by the addition of 5 mg of Alcalase-CLEA. A sample (2 ml) was taken after two hours. 2 ml of acetonitrile was added and the mixture was centrifuged. The supernatants were analyzed by HPLC. The results are shown in Table 2.

TABLE 2

| | | Composition reaction mixture | | |
|---|---|---|---|---|
| Ex. | Ammonium source | Z-Ala-Phe-NH$_2$ a/a % | Z-Ala-Phe-OH a/a % | Z-Ala-Phe-OMe a/a % |
| 2 | (NH$_4$)$_2$CO$_3$ | 11.8 | 6.8 | 81.3 |
| 3 | NH$_2$CO$_2$NH$_4$ | 16.1 | 8.7 | 75.2 |
| H | NH$_4$Cl | 0.4 | 7.2 | 92.4 |

Example 4

Procedure for Enzymatic Amidation of a Tripeptide

A stock solution of Z-Ala-Phe-Ala-OMe in DMF (200 mM) was prepared. 0.5 mmol of NH$_2$CO$_2$NH$_4$ was added to 0.25 ml of the tripeptide stock solution. 0.625 ml DMF and 4.125 ml Bu$^t$OH was added. The reaction mixture was incubated at 30° C. and the reaction was started by the addition of 20 mg of Alcalase-CLEA. A sample (2 ml) was taken after two hours and after four hours. 2 ml of acetonitrile was added and the mixture was centrifuged. The supernatants were analyzed by HPLC. The results are presented in Table 3.

TABLE 3

| Time (hours) | Z-Ala-Phe-Ala-NH$_2$ a/a % | Z-Ala-Phe-Ala-OH a/a % | Z-Ala-Phe-Ala-OMe a/a % |
|---|---|---|---|
| 2 | 69.7 | 10.2 | 18.3 |
| 4 | 79.0 | 10.6 | 8.9 |

Example 5

Effect of "Dry" Environment on the Amidation of a Dipeptide with Free Subtilisin All solvents were dried with mol sieves prior to the experiment.

A stock solution of Z-Ala-Phe-OMe in DMF (200 mM) was prepared. 0.5 mmol of ammonium carbamate was added to 0.25 ml of the dipeptide stock solution. 0.625 ml DMF and 4.125 ml Bu$^t$OH was added. The reaction mixture was incubated at 30° C. and the reaction was started by the addition of 1 mg of enzyme Subtilisin A. A sample (2 ml) was taken after two hours. 2 ml of acetonitrile was added and the mixture was centrifuged. The supernatants were analyzed by HPLC. The results are shown in Table 4.

TABLE 4

| Water/Bu$^t$OH/DMF | Z-Ala-Phe-NH$_2$ a/a % | Z-Ala-Phe-OH a/a % | Z-Ala-Phe-OMe a/a % |
|---|---|---|---|
| 0/82.5/17.5 | 1.7 | 0.4 | 97.9 |

Examples 6 to 14

Effect of Additional Ammonium Carbamate and/or Enzyme on the Amidation of a Dipeptide when Subtilisin A is Used A stock solution of Z-Ala-Phe-OMe in DMF (200 mM) was prepared. 0.5 mmol of ammonium carbamate was added to 0.25 ml of the dipeptide stock solution. DMF and Bu$^t$OH was added corresponding to the ratio given in Table 5, for a total reaction volume of 5 ml. The reaction mixture was incubated at 30° C. and the reaction was started by the addition of 10 µl of enzyme solution (20 mg Subtilisin A in 200 µl phosphate buffer 0.1 M pH 7.0) (Initial conditions: 10 mM Z-Ala-Phe-OMe, 100 mM NH$_2$COONH$_4$, pH 7, 30° C.). A sample (2 ml) was taken after 1.5 hours for experiments 6, 9, and 12, and after 3 hours for experiments 7, 8, 10, 11, 13, and 14. 2 ml of acetonitrile was added and the mixture was centrifuged. The supernatants were analyzed by HPLC. The results are shown in Table 5.

TABLE 5

| Ex. | H$_2$O/Bu$^t$OH/DMF | Z-Ala-Phe-NH$_2$ a/a % | Z-Ala-Phe-OH a/a % | Z-Ala-Phe-OMe a/a % | Comments |
|---|---|---|---|---|---|
| 6 | 0.2/82.5/17.5 | 62.1 | 11.6 | 26.2 | |
| 7 | 0.2/82.5/17.5 | 75 | 10.7 | 14.2 | extra carbamate (0.5 mmol at 1.5 h) |
| 8 | 0.2/82.5/17.5 | 77.2 | 12.3 | 10.6 | extra carbamate (0.5 mmol) & enzyme (10 µl) at 1.5 h |
| 9 | 0.2/70/30 | 67.3 | 9.6 | 23.1 | |
| 10 | 0.2/70/30 | 75.8 | 9.3 | 14.9 | extra carbamate (0.5 mmol at 1.5 h) |
| 11 | 0.2/70/30 | 81.7 | 10.9 | 7.5 | extra carbamate (0.5 mmol) & enzyme (10 µl) at 1.5 h |
| 12 | 0.2/40/60 | 53.6 | 7.2 | 39.1 | |
| 13 | 0.2/40/60 | 56.5 | 6.3 | 37.2 | extra carbamate (0.5 mmol at 1.5 h) |
| 14 | 0.2/40/60 | 68.6 | 8.4 | 23 | extra carbamate (0.5 mmol) & enzyme (10 µl) at 1.5 h |

The results show that addition of extra ammonium carbamate and/or enzyme results in an increase in substrate conversion and formation of higher amounts of amide.

Examples 15 to 18

Effect of Additional Ammonium Carbamate on the Amidation of a Dipeptide when Alcalase CLEA is Used A stock solution of Z-Ala-Phe-OMe in DMF (200 mM) was prepared. 0.5 mmol of the ammonium source was added to 0.25 ml of the dipeptide stock solution. 0.625 ml DMF and 4.125 ml Bu$^t$OH was added. 10 µl phosphate buffer 0.1 M pH 7.0 was added in experiments 17 and 18. The reaction mixture was incubated at 30° C. and the reaction was started by the addition of approximately 20 mg of Alcalase-CLEA. A sample (2 ml) was taken after two hours. 2 ml of acetonitrile was added and the mixture was centrifuged. The supernatants were analyzed by HPLC. The results are shown in Table 6 (initial conditions: 10 mM Z-Ala-Phe-OMe, 100 mM NH$_2$COONH$_4$, pH 7, 30° C.).

TABLE 6

| Ex. | H$_2$O/Bu$^t$OH/DMF | Z-Ala-Phe-NH$_2$ a/a % | Z-Ala-Phe-OH a/a % | Z-Ala-Phe-OMe a/a % | Comments |
|---|---|---|---|---|---|
| 15 | 0/82.5/17.5 | 90.9 | 8.4 | 0.7 | |
| 16 | 0/82.5/17.5 | 91.1 | 7.8 | 1.1 | extra carbamate (0.05 mmol at 1 h) |
| 17 | 0.2/82.5/17.5 | 84.7 | 14.4 | 0.9 | |
| 18 | 0.2/82.5/17.5 | 78.9 | 20.1 | 1 | extra carbamate (0.05 mmol at 1 h) |

The results show that Alcalase CLEA is highly efficient under the conditions tested. 99% of Z-Ala-Phe-OMe was converted. When no additional buffer was added to the reaction mixture, the product contained approx. 91% Z-Ala-Phe-NH$_2$ and 8% free Z-Ala-Phe-OH. Addition of water increases ester hydrolysis yielding the free acid.

Examples 19 and 20

Effect of Additional DMF on the Amidation of a Dipeptide when Alcalase CLEA is Used A stock solution of Z-Ala-Phe-OMe in DMF (200 mM) was prepared. 0.5 mmol of the ammonium source was added to 0.25 ml of the dipeptide stock solution. DMF and Bu$^t$OH was added corresponding to the ratio given in Table 5, for a total reaction volume of 5 ml. The reaction mixture was incubated at 30° C. and the reaction was started by the addition of approximately 20 mg of Alcalase-CLEA. A sample (2 ml) was taken after two hours. 2 ml of acetonitrile was added and the mixture was centrifuged. The supernatants were analyzed by HPLC. The results are shown in Table 7 (initial conditions: 10 mM Z-Ala-Phe-OMe, 100 mM NH$_2$COONH$_4$, pH 7, 30° C.).

TABLE 7

| Ex. | H$_2$O/Bu$^t$OH/DMF | Z-Ala-Phe-NH$_2$ a/a % | Z-Ala-Phe-OH a/a % | Z-Ala-Phe-OMe a/a % |
|---|---|---|---|---|
| 19 | 0/70/30 | 91.4 | 7.6 | 1.1 |
| 20 | 0/60/40 | 91 | 7.4 | 1.6 |

Examples 21 to 30

General Procedure for Screening Different Substrates with Alcalase CLEA and Ammonium Carbamate In a typical experiment, the assay mixture contained approximately 10 mM substrate and 100 mM ammonium carbamate in an anhydrous solvent mixture of 17.5% (vol/vol) DMF in Bu$^t$OH in a total reaction volume of 5 ml. The reaction mixture was thermostated at 30° C. The reaction was initiated by the addition of 4 mg/ml of Alcalase-CLEA. Reaction was incubated at 30° C. for 75 hours. Aliquot samples were taken at 2 h, 4 h and 75 h and the reaction was stopped by the addition of an equal volume of acetonitrile. Samples were analyzed by HPLC. All experiments were performed in duplo.

TABLE 8

| Ex. | Peptide substrate | Reaction time (h) | P—NH$_2$ a/a % | P—OH a/a % | P—OMe a/a % |
|---|---|---|---|---|---|
| 21 | Z-Val-Phe-OMe | 2 | 77.0 | 16.4 | 6.7 |
|  |  | 4 | 82.1 | 17.2 | 6.7 |
|  |  | 75 | 86.7 | 13.4 | 0.0 |
| 22 | Z-Val-Tyr-OMe | 2 | 41.2 | 13.1 | 45.8 |
|  |  | 4 | 44.4 | 20.0 | 35.7 |
|  |  | 75 | 59.3 | 40.0 | 0.8 |
| 23 | Z-Val-Leu-OMe | 2 | 73.4 | 19.5 | 7.2 |
|  |  | 4 | 73.5 | 26.5 | 0.0 |
| 24 | Z-Val-Thr-OMe | 2 | 87.4 | 7.7 | 5.0 |
|  |  | 4 | 90.8 | 9.2 | 0.0 |
| 25 | Z-Val-Ala-OMe | 2 | 88.9 | 11.2 | 0.0 |
| 26 | Z-Val-Met-OMe | 2 | 71.1 | 28.1 | 0.9 |
|  |  | 4 | 72.8 | 27.3 | 0.0 |
| 27 | Z-Val-Lys(Boc)-OMe | 2 | 22.9 | 7.2 | 70.0 |
|  |  | 4 | 33.1 | 12.2 | 54.7 |
|  |  | 75 | 74.8 | 24.0 | 1.3 |
| 28 | Z-Ala-Phe-OMe | 2 | 91.7 | 6.7 | 1.7 |
|  |  | 4 | 92.9 | 6.7 | 0.5 |
| 29 | Z-Ala-Phe-Ala-OMe | 2 | 82.8 | 8.5 | 8.8 |
|  |  | 4 | 92.2 | 6.9 | 1.0 |
| 30 | Z-Ala-Phe-D-Ala-OMe | 2 | 6.0 | 0.3 | 93.7 |
|  |  | 4 | 10.8 | 0.8 | 88.5 |
|  |  | 75 | 35.4 | 10.4 | 54.3 |

With the exception of Z-Val-Tyr-OMe, Z-Val-Lys(Boc)-OMe and Z-Ala-Phe-D-Ala-OMe, all substrate peptides were quantitatively converted into products, i.e. the corresponding amide peptide and free carboxylic acid peptide, in 4 h reaction time. At longer reaction times also the methyl ester peptides ending with Tyr and Lys(Boc) were totally converted. Surprisingly, the methyl ester of the tripeptide with a C-terminal D-Ala residue was also converted. The HPLC analysis at 75 h reaction time showed conversion of 54 ala % of substrate to yield about 36 a/a % of the product Z-Ala-Phe-D-Ala-NH$_2$.

Examples 31 to 45 and Comparative Example I

General Procedure for Screening the Effect of Different Ammonium Salts

In a typical experiment, the assay mixture contained approximately 10 mM peptide ester Z-Ala-Phe-OMe and 100 mM ammonium salt in an anhydrous solvent mixture of 17.5% (vol/vol) DMF in Bu$^t$OH in a total reaction volume of 5 ml. The reaction mixture was thermostated at 30° C. The reaction was initiated by the addition of the enzyme (Alcalase-CLEA: 4 mg/ml or Subtilisin A (from SigmaAldrich): 1 mg/ml). Reaction was incubated at 30° C. for 21 hours. Aliquot samples were taken at 2 h, 4 h and 21 h and the reaction was stopped by the addition of an equal volume of acetonitrile. Samples were analyzed by HPLC. All experiments were performed in duplo. The results for Alcalase CLEA are shown in Table 9. The results for Subtilisin A are shown in Table 10.

TABLE 9

(Alcalase CLEA)

| Ex. | Ammonium salt | Reaction time h | Z-Ala-Phe-NH$_2$ a/a % | Z-Ala-Phe-OH a/a % | Z-Ala-Phe-OMe a/a % |
|---|---|---|---|---|---|
| 31 | NH$_2$COONH$_4$ Carbamate | 2 | 92.3 | 7.7 | 0 |
|  |  | 4 | 92.3 | 7.7 | 0 |
|  |  | 21 | 91.4 | 8.6 | 0 |
| 32 | CH$_3$COONH$_4$ Acetate | 2 | 83.4 | 12.5 | 4.1 |
|  |  | 4 | 87.2 | 12.3 | 0.5 |
|  |  | 21 | 91.2 | 8.8 | 0 |
| 33 | (NH$_4$)$_2$CO$_3$ Carbonate | 2 | 88.1 | 11.9 | 0.0 |
|  |  | 4 | 88.8 | 11.2 | 0.0 |
|  |  | 21 | 90.8 | 9.2 | 0 |
| 34 | NH$_4$HCO$_3$ Bicarbonate | 2 | 84.7 | 14.9 | 0.4 |
|  |  | 4 | 85.7 | 14.3 | 0 |
|  |  | 21 | 88.3 | 11.7 | 0 |
| 35 | C$_6$H$_5$COONH$_4$ Benzoate | 2 | 61.1 | 30.4 | 8.5 |
|  |  | 4 | 68.7 | 29.8 | 1.5 |
|  |  | 21 | 87.7 | 12.3 | 0 |
| 36 | HCOONH$_4$ Formate | 2 | 31.6 | 19.8 | 48.5 |
|  |  | 4 | 41.9 | 26.6 | 31.5 |
|  |  | 21 | 69.5 | 30.5 | 0 |
| 37 | NH$_4$F Fluoride | 2 | 26.9 | 15.1 | 57.9 |
|  |  | 4 | 41.2 | 20.5 | 38.2 |
|  |  | 21 | 71.0 | 27.0 | 1.9 |
| 38 | (NH$_4$)$_3$C$_6$H$_5$O$_7$ Citrate | 2 | 5.6 | 47.9 | 46.4 |
|  |  | 4 | 12.6 | 61.0 | 26.4 |
|  |  | 21 | 77.6 | 22.4 | 0 |
| 39 | (NH$_4$)$_2$C$_2$O$_4$•H$_2$O Oxalate monohydrate | 2 | 3.7 | 48.2 | 48.1 |
|  |  | 4 | 10.5 | 62.9 | 26.6 |
|  |  | 21 | 68.1 | 31.9 | 0 |
| 40 | (NH$_4$)$_2$C$_4$H$_4$O$_6$ Tartrate | 2 | 6.3 | 37.7 | 55.9 |
|  |  | 4 | 17.6 | 50.8 | 31.6 |
|  |  | 21 | 68.2 | 31.8 | 0 |
| 41 | (NH$_4$)$_2$SO$_3$•H$_2$O Sulphite hydrate | 2 | 2.9 | 6.1 | 91.0 |
|  |  | 4 | 7.2 | 12.8 | 80.0 |
|  |  | 21 | 60.7 | 39.3 | 0 |
| I | NH$_4$Cl Chloride | 2 | 6.8 | 38.8 | 54.4 |
|  |  | 4 | 14.8 | 52.9 | 32.3 |
|  |  | 21 | 68.5 | 31.5 | 0 |

Ammonium carbamate, ammonium acetate, ammonium carbonate, ammonium bicarbonate, and ammonium benzoate show excellent performance.

TABLE 10

(Subtilisin A)

| Ex. | Ammonium source | Reaction time, h | Z-Ala-Phe-NH$_2$ a/a % | Z-Ala-Phe-OH a/a % | Z-Ala-Phe-OMe a/a % |
|---|---|---|---|---|---|
| 42 | NH$_2$COONH$_4$ Carbamate | 2 | 36.9 | 4.8 | 48.4 |
|  |  | 4 | 60.2 | 8.2 | 31.6 |
|  |  | 21 | 86.8 | 12.9 | 0.3 |
| 43 | CH$_3$COONH$_4$ Acetate | 2 | 42.4 | 7.9 | 49.7 |
|  |  | 4 | 58.6 | 11.6 | 29.8 |
|  |  | 21 | 82.1 | 17.1 | 0.8 |
| 44 | NH$_4$HCO$_3$ Bicarbonate | 2 | 27.2 | 9.8 | 62.9 |
|  |  | 4 | 46.6 | 16.1 | 37.3 |
|  |  | 21 | 76.0 | 23.7 | 0.3 |
| 45 | (NH$_4$)$_2$CO$_3$ Carbonate | 2 | 42.4 | 7.9 | 49.7 |
|  |  | 4 | 53.1 | 12.0 | 34.9 |
|  |  | 21 | 80.9 | 8.7 | 0.4 |

Table 10 shows the results of the conversion of Z-Ala-Phe-OMe into amide with Subtilisin A, with ammonium carbamate, ammonium acetate, ammonium bicarbonate and ammonium carbonate as source of ammonia. High substrate conversion is obtained after 21 h reaction for the selected salts. Highest yield (i.e. 86%) of the amide Z-Ala-Phe-NH$_2$ was obtained for ammonium carbamate at a reaction time of 21 h. More product of the ester hydrolysis is obtained for free Subtilisin A as compared to Alcalase-CLEA.

Examples 46 to 53

General Procedure for Screening Different Substrates with Subtilisin A and Ammonium Carbamate In a typical experiment, the assay mixture contained approximately 10 mM peptide ester and 100 mM ammonium carbamate in an anhydrous solvent mixture of 17.5% (vol/vol) DMF in Bu$^t$OH in a total reaction volume of 5 ml. The reaction mixture was thermostated at 30° C. The reaction was initiated by the addition of 1 mg/ml of Subtilisin A (from Sigma Aldrich). Reaction was incubated at 30° C. for 21 hours. Aliquot samples were taken at 2 h, 4 h and 21 h and the reaction was stopped by the addition of an equal volume of acetonitrile. Samples were analyzed by HPLC. All experiments were, performed in duplicate. Results are given in Table 11.

TABLE 11

| Ex. | Peptide substrate | Reaction time, h | P—NH$_2$ a/a % | P—OH a/a % | P—OMe a/a % |
|---|---|---|---|---|---|
| 46 | Z-Val-Phe-OMe | 2 | 14.8 | 5.6 | 79.6 |
|  |  | 4 | 26.9 | 10.7 | 62.4 |
|  |  | 21 | 61.0 | 29.1 | 9.9 |
| 47 | Z-Val-Tyr-OMe | 2 | 5.8 | 3.0 | 91.2 |
|  |  | 4 | 11.1 | 5.6 | 83.3 |
|  |  | 21 | 29.6 | 18.3 | 52.1 |
| 48 | Z-Val-Leu-OMe | 2 | 14.3 | 6.9 | 78.8 |
|  |  | 4 | 25.9 | 12.1 | 62.0 |
|  |  | 21 | 58.0 | 33.7 | 8.3 |
| 49 | Z-Val-Thr-OMe | 2 | 18.2 | 2.3 | 79.4 |
|  |  | 4 | 34.4 | 4.5 | 61.1 |
|  |  | 21 | 76.7 | 13.7 | 9.6 |
| 50 | Z-Val-Ala-OMe | 2 | 50.1 | 10.0 | 39.9 |
|  |  | 4 | 70.0 | 14.4 | 15.6 |
|  |  | 21 | 82.1 | 17.9 | 0.0 |
| 51 | Z-Val-Met-OMe | 2 | 27.5 | 7.8 | 64.7 |
|  |  | 4 | 42.3 | 15.6 | 42.2 |
|  |  | 21 | 55.7 | 44.3 | 0.0 |
| 52 | Z-Val-Lys(Boc)-OMe | 2 | 1.6 | 0.0 | 98.4 |
|  |  | 4 | 2.9 | 1.2 | 95.9 |
|  |  | 21 | 10.5 | 6.7 | 82.7 |
| 53 | Z-Ala-Phe-OMe | 2 | 36.9 | 4.8 | 58.4 |
|  |  | 4 | 60.2 | 8.2 | 31.6 |
|  |  | 21 | 86.8 | 12.9 | 0.3 |

The specificity of Alcalase CLEA for various terminal amino acids was reported in Examples 21 to 30. Here, the results are reported obtained for testing the substrate specificity of soluble subtilisin. All peptide substrates were transformed into amides, but with lower amide yields than in the case of Alcalase-CLEA. Best substrates were Z-Ala-Phe-OMe (86.8% amide after 21 h) and Z-Val-Ala-OMe (82% amide formed after 21 h), while Z-Val-Lys(Boc)-OMe was the worse substrate. Extensive ester hydrolysis was observed. It appears that Alcalase CLEA and Subtilisin A have slightly different substrate specificity.

Examples 54 to 68

General Procedure for Screening Different Polar Organic Solvents

In a typical experiment, the assay mixture contained approximately 10 mM Z-Ala-Phe-OMe and 100 mM ammonium carbamate in an anhydrous solvent mixture containing 82.5% dry Bu$^t$OH or Am$^t$OH and 17.5% (vol/vol) of a co-solvent. The total reaction volume was 5 ml. The reaction mixture was thermostated at 30° C. The reaction was initiated by the addition of the enzyme (Alcalase-CLEA: 4 mg/ml or Subtilisin A (Sigma Aldrich): 1 mg/ml). Reaction was incubated at 30° C. for 22 hours. Aliquot samples were taken at 2 h, 4 h and 22 h and the reaction was stopped by the addition of an equal volume of acetonitrile. Samples were analyzed by HPLC. All experiments were performed in duplicate. The results for Alcalase CLEA are shown in Table 12. The results for Subtilisin A are shown in Table 13.

TABLE 12

(Alcalase CLEA)

| Ex. | Solvent (82.5:17.5 (% vol/vol)) | Reaction time h | Z-Ala-Phe-NH$_2$ a/a % | Z-Ala-Phe-OH a/a % | Z-Ala-Phe-OMe a/a % |
|---|---|---|---|---|---|
| 54 | Bu$^t$OH/DMF | 2 | 92.0 | 8.0 | 0.0 |
|  |  | 4 | 92.1 | 7.9 | 0.0 |
|  |  | 22 | 91.3 | 8.7 | 0.0 |
| 55 | Bu$^t$OH/NMP | 2 | 90.0 | 7.6 | 2.4 |
|  |  | 4 | 91.9 | 7.8 | 0.3 |
|  |  | 22 | 91.3 | 8.7 | 0.0 |
| 56 | Bu$^t$OH/dioxane | 2 | 88.5 | 8.2 | 3.2 |
|  |  | 4 | 91.3 | 8.2 | 0.4 |
|  |  | 22 | 92.2 | 7.8 | 0.0 |
| 57 | Bu$^t$OH/DMA | 2 | 92.0 | 7.6 | 0.5 |
|  |  | 4 | 92.2 | 7.8 | 0.0 |
|  |  | 22 | 90.3 | 9.7 | 0.0 |
| 58 | Bu$^t$OH/DCM | 2 | 87.1 | 10.3 | 2.6 |
|  |  | 4 | 89.1 | 10.6 | 0.3 |
|  |  | 22 | 91.7 | 8.3 | 0.0 |
| 59 | Bu$^t$OH/THF | 2 | 91.5 | 7.8 | 0.7 |
|  |  | 4 | 92.3 | 7.7 | 0.0 |
|  |  | 22 | 93.3 | 6.7 | 0.0 |
| 60 | Bu$^t$OH/CH$_3$CN | 2 | 91.5 | 8.5 | 0.0 |
|  |  | 4 | 91.7 | 8.3 | 0.0 |
|  |  | 22 | 91.5 | 8.2 | 0.0 |
| 61 | Bu$^t$OH/DCE | 2 | 89.7 | 9.3 | 1.0 |
|  |  | 4 | 90.4 | 9.6 | 0.0 |
|  |  | 22 | 89.0 | 10.6 | 0.3 |
| 62 | Am$^t$OH/DMF* | 2 | 78.0 | 4.4 | 17.7 |
|  |  | 4 | 89.9 | 5.5 | 4.6 |
|  |  | 22 | 94 | 6 | 0 |
| 63 | Am$^t$OH/NMP* | 2 | 48.1 | 2.8 | 49.0 |
|  |  | 4 | 65.8 | 4.5 | 29.7 |
|  |  | 22 | 90.4 | 8.7 | 0.9 |

*Alcalase CLEA concentration: 1 mg enzyme/ml reaction mixture. In all other experiments, the enzyme was used in concentration of 4 mg/ml.

TABLE 13

(Subtilisin A)

| Ex. | Solvent (82.5:17.5 (% vol/vol)) | Reaction time h | Z-Ala-Phe-NH$_2$ a/a % | Z-Ala-Phe-OH a/a % | Z-Ala-Phe-OMe a/a % |
|---|---|---|---|---|---|
| 64 | Bu$^t$OH/DMF | 2 | 36.9 | 4.8 | 58.4 |
|  |  | 4 | 60.2 | 8.2 | 31.6 |
|  |  | 21 | 86.8 | 12.9 | 0.3 |
| 65 | Bu$^t$OH/NMP | 2 | 25.1 | 3.4 | 71.5 |
|  |  | 4 | 43 | 6 | 51 |
|  |  | 21 | 83.3 | 13.5 | 3.2 |
| 66 | Bu$^t$OH/dioxane | 2 | 9.9 | 1.4 | 88.6 |
|  |  | 4 | 16.3 | 2.4 | 81.3 |
|  |  | 21 | 44.6 | 7.5 | 47.9 |
| 67 | Bu$^t$OH/THF | 2 | 23.4 | 3.3 | 73.3 |
|  |  | 4 | 36 | 5.2 | 58.8 |
|  |  | 21 | 70.3 | 12.1 | 17.6 |
| 68 | Am$^t$OH/DMF | 2 | 22.2 | 3.5 | 74.3 |
|  |  | 4 | 36.9 | 6.1 | 57 |
|  |  | 21 | 73.4 | 21.1 | 5.4 |

Table 12 shows the results obtained for screening solvent effects when using Alcalase CLEA as catalyst. After 2 hours incubation, in experiments containing solvent mixtures of 82.5 Bu$^t$OH/17.5x (% vol/vol), when high amount of Alcalase CLEA was used (i.e. 4 mg enzyme/ml reaction mixture) total substrate conversion was obtained for all solvent combination used. The reaction mixture contained more than 87% amide, and the amide yield increased above 93% at longer reaction time.

Am$^t$OH proves to be an excellent solvent for the amidation of peptide methyl esters. When mixtures of Am$^t$OH/DMF (82.5/17.5 vol/vol) were used as solvent mixture, even at a lower enzyme concentration (Alcalase CLEA added approximately 1 mg enzyme/ml reaction mixture), high yields of amide (i.e. about 80% amide) were obtained after 2 hours of incubation. At longer reaction time, at total substrate conversion, the product mixture contained more than 90% amide. This suggests that Am$^t$OH can replace the Bu$^t$OH as main co-solvent in the reaction mixture for enzymatic amidation of methyl esters of peptides. Similar trends were obtained when Subtilisin A was used (Table 13). However, Subtilisin A performs less than Alcalase CLEA in amide synthesis. About 85% amide is obtained after 21 hours in 82.5 Bu$^t$OH/17.5 DMF (% vol/vol). Generally, the amount of free peptide resulted from ester hydrolysis is higher, around 12-15%. Binary solvent mixtures containing 82.5% Bu$^t$OH or Am$^t$OH in combination with 17.5% of either DMF and NMP seem to be the best solvent mixtures for Subtilisin A in amide synthesis.

Examples 69 to 82

Since Am$^t$OH seemed to be a very good co-solvent in combination with DMF and NMP for the enzymatic amidation reaction as shown in Examples 55 to 69, these solvent mixtures were tested with the same procedure for some model reactions with Alcalase CLEA and Subtilisin A, for different peptide substrates and ammonium salts, respectively. Results are given in Table 14 for Alcalase CLEA (1 mg/ml) and Table 15 for Subtilisin A (0.2 mg/ml). The conclusion of these experiments is that Am$^t$OH can be used to replace Bu$^t$OH as cosolvent.

TABLE 14

(Alcalase CLEA)

| Ex. | Reaction time, h | Ammonium salt | Peptide Substrate | Solvent (82.5:17.5) | % P—NH$_2$ | % P—OH | % P—OMe |
|---|---|---|---|---|---|---|---|
| 69 | 2 | NH$_2$COONH$_4$ | Z-Ala-Phe-OMe | Am$^t$OH/DMF | 78.0 | 4.4 | 17.7 |
|  | 4 |  |  |  | 89.9 | 5.5 | 4.6 |
|  | 21 |  |  |  | 94.0 | 6.0 | 0.0 |
| 70 | 2 | NH$_2$COONH$_4$ | Z-Val-Thr-OMe | Am$^t$OH/DMF | 47.9 | 2.8 | 49.3 |
|  | 4 |  |  |  | 64.8 | 4.6 | 30.6 |
|  | 21 |  |  |  | 80.3 | 14.6 | 5.1 |
| 71 | 2 | NH$_2$COONH$_4$ | Z-Val-Ala-OMe | Am$^t$OH/DMF | 78.5 | 8.6 | 12.9 |
|  | 4 |  |  |  | 86.2 | 9.9 | 4.0 |
|  | 21 |  |  |  | 87.6 | 10.6 | 1.8 |
| 72 | 2 | NH$_2$COONH$_4$ | Z-Ala-Phe-OMe | Am$^t$OH/NMP | 48.1 | 2.8 | 49.0 |
|  | 4 |  |  |  | 65.8 | 4.5 | 29.7 |
|  | 21 |  |  |  | 90.4 | 8.7 | 0.9 |
| 73 | 2 | NH$_2$COONH$_4$ | Z-Val-Thr-OMe | Am$^t$OH/NMP | 39.4 | 2.0 | 58.5 |
|  | 4 |  |  |  | 57.1 | 3.7 | 39.3 |
|  | 21 |  |  |  | 85.7 | 10.4 | 3.9 |
| 74 | 2 | NH$_2$COONH$_4$ | Z-Val-Ala-OMe | Am$^t$OH/NMP | 60.1 | 7.7 | 32.2 |
|  | 4 |  |  |  | 74.7 | 10.3 | 14.9 |
|  | 21 |  |  |  | 85.3 | 13.1 | 1.6 |
| 75 | 2 | NH$_2$COONH$_4$ | Z-Ala-Phe-OMe | Am$^t$OH/DMF | 78 | 4.4 | 17.7 |
|  | 4 |  |  |  | 89.9 | 5.5 | 4.6 |
|  | 21 |  |  |  | 94 | 6 | 0 |
| 76 | 2 | (NH$_4$)$_2$CO$_3$ | Z-Ala-Phe-OMe | Am$^t$OH/DMF | 68.7 | 6.1 | 25.2 |
|  | 4 |  |  |  | 83.5 | 8.1 | 8.3 |
|  | 21 |  |  |  | 90.9 | 9.1 | 0 |
| 77 | 2 | CH$_3$COONH$_4$ | Z-Ala-Phe-OMe | Am$^t$OH/DMF | 39 | 2.6 | 58.4 |
|  | 4 |  |  |  | 52.8 | 3.9 | 43.3 |
|  | 21 |  |  |  | 86 | 9.9 | 4.1 |

TABLE 15

(Subtilisin A)

| Ex. | Reaction time h | Ammonium salt | Peptide Substrate | Solvent (82.5:17.5) | % P—NH$_2$ | % P—OH | % P—OMe |
|---|---|---|---|---|---|---|---|
| 78 | 2 | NH$_2$COONH$_4$ | Z-Val-Thr-OMe | Am$^t$OH/DMF | 10.9 | 1.9 | 873 |
|  | 4 |  |  |  | 21.2 | 3.4 | 75.4 |
|  | 21 |  |  |  | 57.0 | 16.5 | 26.5 |
| 79 | 2 | NH$_2$COONH$_4$ | Z-Val-Ala-OMe | Am$^t$OH/DMF | 31.0 | 8.7 | 60.3 |
|  | 4 |  |  |  | 49.7 | 14.1 | 36.2 |
|  | 21 |  |  |  | 73.6 | 24.2 | 2.2 |
| 80 | 2 | NH$_2$COONH$_4$ | Z-Ala Phe-OMe | Am$^t$OH/DMF | 22.2 | 3.5 | 74.3 |
|  | 4 |  |  |  | 36.9 | 6.1 | 57.0 |
|  | 21 |  |  |  | 73.4 | 21.1 | 5.4 |

TABLE 15-continued (Subtilisin A)

| Ex. | Reaction time h | Ammonium salt | Peptide Substrate | Solvent (82.5:17.5) | % P—NH$_2$ | % P—OH | % P—OMe |
|---|---|---|---|---|---|---|---|
| 81 | 2 | (NH$_4$)$_2$CO$_3$ | Z-Ala Phe-OMe | Am$^t$OH/DMF | 24.9 | 6.5 | 68.6 |
|  | 4 |  |  |  | 32.0 | 9.2 | 58.8 |
|  | 21 |  |  |  | 69.1 | 26.5 | 4.4 |
| 82 | 2 | CH$_3$COONH$_4$ | Z-Ala Phe-OMe | Am$^t$OH/DMF | 30.3 | 5.8 | 63.9 |
|  | 4 |  |  |  | 45.2 | 9.7 | 45.1 |
|  | 21 |  |  |  | 73.7 | 21.0 | 5.3 |

Examples 83 to 91

Optimizing the Amount of Alcalase CLEA in the Reaction Mixture

Previous experiments showed that Alcalase CLEA is very efficient in the amide synthesis. Experiments were performed to determine the lowest enzyme concentration that can be used in the reaction, to obtain high product yield in a reasonable reaction time.

In a typical experiment, the assay mixture contained approximately 10 mM peptide substrate and 100 mM ammonium carbamate in an anhydrous solvent mixture of 82.5% Bu$^t$OH and 17.5% (vol/vol) of DMF, in a total reaction volume of 5 ml. The reaction mixture was thermostated at 30° C. The reaction was initiated by the addition of the enzyme (Alcalase-CLEA: 0.2 mg/ml, 1 mg/ml and 2 mg/ml, respectively). Reaction was incubated at 30° C. for 21 hours. Aliquot samples were taken at 2 h, 4 h and 21 h and the reaction was stopped by the addition of an equal volume of acetonitrile. Samples were analyzed by HPLC. All experiments were performed in duplicate. The results are listed in Table 16.

TABLE 16

| Ex. | Reaction time, h | Enzyme concentration, mg/ml | % P—NH$_2$ | % P—OH | % P—OMe |
|---|---|---|---|---|---|
| Z-Ala-Phe-OMe |  |  |  |  |  |
| 83 | 2 | 0.2 | 33.5 | 1.2 | 65.3 |
|  | 4 | 0.2 | 51.7 | 2.4 | 45.9 |
|  | 21 | 0.2 | 85 | 6.4 | 8.6 |
| 84 | 2 | 1 | 80.4 | 3.4 | 16.2 |
|  | 4 | 1 | 92.3 | 4.2 | 3.5 |
|  | 21 | 1 | 95.1 | 4.9 | 0 |
| 85 | 2 | 2 | 91.1 | 5.4 | 3.6 |
|  | 4 | 2 | 94.5 | 5.5 | 0 |
|  | 21 | 2 | 94 | 6 | 0 |
| Z-Val-Phe-OMe |  |  |  |  |  |
| 86 | 2 | 0.2 | 14.5 | 1.3 | 84.1 |
|  | 4 | 0.2 | 24.2 | 2.5 | 73.3 |
|  | 21 | 0.2 | 55.7 | 11.4 | 32.9 |
| 87 | 2 | 1 | 49.8 | 5.2 | 44.9 |
|  | 4 | 1 | 67.8 | 7.6 | 24.6 |
|  | 21 | 1 | 87.8 | 11.8 | 0.4 |
| 88 | 2 | 2 | 69.5 | 9.7 | 20.8 |
|  | 4 | 2 | 81.7 | 11.7 | 6.6 |
|  | 21 | 2 | 88.4 | 11.6 | 0.0 |
| Z-Val-Thr-OMe |  |  |  |  |  |
| 89 | 2 | 0.2 | 56.7 | 2.6 | 40.7 |
|  | 4 | 0.2 | 76.4 | 3.9 | 19.7 |
|  | 21 | 0.2 | 93.5 | 6.5 | 0.0 |
| 90 | 2 | 1.2 | 76.4 | 3.9 | 19.7 |
|  | 4 | 1.2 | 76.4 | 3.9 | 19.7 |
|  | 21 | 1.2 | 93.5 | 6.5 | 0.0 |
| 91 | 2 | 2 | 68.8 | 4.2 | 27.0 |
|  | 4 | 2 | 84.1 | 5.8 | 10.0 |
|  | 21 | 2 | 90.3 | 9.7 | 0.0 |

It can be seen that at an Alcalase CLEA concentration of 1 mg/ml reaction mixture, 95% conversion of the substrate Z-Ala-Phe-OMe is obtained after 4 hours incubation. The product mixture contained 92% amide and only 3.5% of the secondary product of the ester hydrolysis. High amide yields were obtained for other peptide substrates, for this low enzyme concentration, but at longer reaction times. However, these results show that the concentration of enzyme, i.e. Alacalse-CLEA, can be reduced significantly, thus making the process more economical.

Example 92

Amidation of Boc-Pro-Pro-Ala-Phe-Ala-OMe

In a typical experiment, the assay mixture contained approximately 10 mM peptide substrate and 100 mM ammonium carbamate in an anhydrous solvent mixture of 82.5% Bu$^t$OH and 17.5% (vol/vol) of DMF, in a total reaction volume of 5 ml. The reaction mixture was thermostated at 30° C. The reaction was initiated by the addition of 4 mg/ml Alcalase CLEA. Reaction was incubated at 30° C. for 21 hours. Aliquot samples were taken at 2 h, 4 h and 21 h and the reaction was stopped by the addition of an equal volume of acetonitrile. Samples were analyzed by HPLC. The results are listed in Table 17.

TABLE 17

| Ex. | Reaction time, h | % P—NH$_2$ | % P—OH | % P—OMe |
|---|---|---|---|---|
| 92 | 2 | 42.15 | 0.3 | 57.55 |
|  | 4 | 60.73 | 0.55 | 38.72 |
|  | 21 | 99.21 | — | 0.79 |

Example 93

Enzymatic Amidation of Z-Ala-Phe-OH

In a typical experiment, the assay mixture contained approximately 10 mM peptide substrate with a C-terminal free acid and 100 mM ammonium carbamate in an anhydrous solvent mixture of 82.5% Bu$^t$OH and 17.5% (vol/vol) of DMF, in a total reaction volume of 5 ml. The reaction mixture was thermostated at 30° C. The reaction was initiated by the addition of 4 mg/ml Alcalase CLEA. Reaction was incubated at 30° C. for 21 hours. Aliquot samples were taken at 2 h, 4 h and 21 h and the reaction was stopped by the addition of an equal volume of acetonitrile. Samples were analyzed by HPLC. The results are listed in Table 18.

TABLE 18

| Ex. | Reaction time, h | Z-Ala-Phe-NH$_2$ a/a % | Z-Ala-Phe-OH a/a % |
|---|---|---|---|
| 93 | 2 | 29.14 | 70.86 |
| | 4 | 34.43 | 65.57 |
| | 21 | 69.86 | 30.14 |

It can be concluded from these experiments that the C-terminal free acid of a peptide substrate can also be amidated by ammonium carbamate in the presence of Alcalase CLEA.

The invention claimed is:

1. A process for the amidation of C-terminal esters or acids of peptide substrates in solution-phase synthesis of peptides, comprising amidating one or more peptide substrates comprising C-terminal esters or acids using the protease subtilisin in any suitable form in the presence of one or more ammonium salts derived from an acid having a pKa above 0.

2. A process according to claim 1, wherein C-terminal esters of peptide substrates are amidated.

3. A process according to claim 2, wherein the esters of the C-terminal esters of the peptide substrate are selected from the group of $C_{1-12}$ (ar)alkyl esters.

4. A process according to claim 3, wherein the esters of the C-terminal esters of the peptide substrate are selected from the group of primary $C_{1-12}$ (ar)alkyl esters.

5. A process according to claim 4, wherein the esters of the C-terminal esters of the peptide substrate are selected from the group of primary $C_{1-4}$ alkyl esters.

6. A process according to claim 5, wherein the ester of the C-terminal ester of the peptide substrate is the C-terminal methyl ester.

7. A process according to claim 1, wherein the ammonium salt is derived from an acid having a pKa above 3.5.

8. A process according to claim 7, wherein the ammonium salt has the following chemical structure (I):

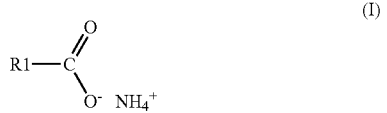

wherein
R1 is selected from the group of hydrogen, $C_{1-12}$ (ar)alkyl, $C_{6-12}$ aryl, —N(R2)$_2$, —OH, and R3-O$^-$NH$_4^+$,
R2 is selected from the group of hydrogen and/or $C_{1-4}$ alkyl, and
R3 is a bond, a carbonyl group, or a $C_{1-4}$ alkyl carbonyl group, optionally substituted with one or more hydroxyl groups and/or —COO$^-$NH$_4^+$,
optionally in hydrated form.

9. A process according to claim 8, wherein R1 is selected from the group of $C_{1-12}$ (ar)alkyl, $C_{6-12}$ aryl, —NH$_2$, —OH, and —O$^-$NH$_4^+$.

10. A process according to claim 9, wherein the ammonium salt is selected from ammonium carbamate, ammonium carbonate, ammonium bicarbonate, ammonium acetate, ammonium benzoate, and mixtures thereof.

11. A process according to claim 10, wherein the ammonium salt is ammonium carbamate.

12. A process according to claim 1, wherein the molar ratio of ammonium salt to peptide substrate ranges from 2:1 to 20:1.

13. The process according to claim 1, wherein the peptide substrate comprising the C-terminal ester or acid comprises a C-terminal acyl residue which is an α-amino acyl residue from natural or synthetic origin.

14. The process according to claim 13, wherein the α-amino acyl residue is selected from Ala, protected Cys, protected Asp, protected Glu, Phe, Gly, His, (protected) Lys, Leu, Met, Asn, Gln, (protected) Arg, (protected) Ser, Thr, Val, (protected) Trp and (protected) Tyr.

15. The process according to claim 1, wherein the peptide substrate is prepared according to a process for rapid solution synthesis of a peptide in an organic solvent or a mixture of organic solvents, the process comprising repetitive cycles of steps (a)-(d):
 a) a coupling step, using an excess of an activated carboxylic component to acylate an amino component,
 b) a quenching step in which a scavenger is used to remove residual activated carboxylic functions, wherein the scavenger may also be used for deprotection of the growing peptide,
 c) one or more aqueous extractions and
 optionally, (d) a separate deprotection step, followed by one or more aqueous extractions,
 whereby in at least one cycle in process step b an amine comprising a free anion or a latent anion is used as a scavenger of residual activated carboxylic functions.

16. The process according to claim 1, wherein the protease subtilisin is of the family EC 3.4.21.62.

17. The process according to claim 1, wherein the protease subtilisin is free subtilisin.

18. The process according to claim 1, wherein the protease subtilisin is cross-linked enzyme aggregate (CLEA) subtilisin.

19. The process according to claim 1, wherein an organic solvent is used.

20. The process according to claim 19, wherein the organic solvent is selected from N,N-dimethylformamide (DMF), N-methyl-2-pyrrolidone (NMP), dioxane, N,N-dimethylacetamide (DMA), dichloromethane (DCM), tetrahydrofuran (THF), acetonitrile, tert-butanol, tert-amyl alcohol, dichloroethane (DCE), tert-butyl methyl ether (MTBE), and mixtures thereof.

21. The process according to claim 20, wherein the organic solvent is a mixture of tert-butanol and DMF, tert-butanol and NMP, tert-amyl alcohol and DMF, or tert-amyl alcohol and NMP.

22. The process according to claim 19, wherein water is present in the organic solvent ranging from 0.0001 to 5% (v/v).

23. The process according to claim 1, wherein pH at which the reaction is performed is selected from the range of 5.5-10.

24. The process according to claim 1, wherein the reaction temperature for the amidation is 15-60° C.

25. The process according to claim 1, wherein the amount of protease subtilisin ranges from 1 to 50 wt. % related to the peptide substrate.

26. The process according to claim 1, wherein the amidation is performed by stepwise adding portions of the protease subtilisin (in any suitable form) into the reaction mixture comprising one or more peptide substrates comprising C-terminal esters or acids.

27. The process according to claim 1, wherein the amidation is performed by stepwise adding portions of the ammonium salt into the reaction mixture comprising one or more peptide substrates comprising C-terminal esters or acids.

* * * * *